US011555567B2

(12) United States Patent
Heighes et al.

(10) Patent No.: US 11,555,567 B2
(45) Date of Patent: Jan. 17, 2023

(54) SANITARY FITTING

(71) Applicant: WilMarc Holdings, LLC, Fort Collins, CO (US)

(72) Inventors: Tyler Heighes, Fort Collins, CO (US); Paul C. Ciccone, Wellington, CO (US)

(73) Assignee: Wilmarc Holdings, LLC, Fort Collins, CO (US)

( * ) Notice: Subject to any disclaimer, the term of this patent is extended or adjusted under 35 U.S.C. 154(b) by 110 days.

(21) Appl. No.: 16/917,535

(22) Filed: Jun. 30, 2020

(65) Prior Publication Data
US 2021/0404585 A1   Dec. 30, 2021

(51) Int. Cl.
*F16L 29/02*   (2006.01)
*F16L 33/035*   (2006.01)

(52) U.S. Cl.
CPC ............. *F16L 29/02* (2013.01); *F16L 33/035* (2013.01)

(58) Field of Classification Search
CPC ........ F16L 29/02; F16L 33/035; A61M 39/12; A61M 2039/1027; A61M 2039/268; A61M 39/00; A61M 39/18; A61M 39/14; A61M 2039/1072; A61M 1/169; A61F 5/4405
USPC ....................................................... 251/148
See application file for complete search history.

(56) References Cited

U.S. PATENT DOCUMENTS 3,595,445 A * 7/1971 Buford .................... B67D 3/042
222/511
4,375,864 A * 3/1983 Savage ................ B65D 77/067
222/499
4,415,085 A    11/1983 Clarke et al.
4,953,592 A    9/1990 Takahashi et al.
5,137,527 A    8/1992 Miller et al.
(Continued)

FOREIGN PATENT DOCUMENTS

AU        678906      * 12/1997
CH        631383 A5  * 10/1978
CN    208761438 U    *  4/2019

OTHER PUBLICATIONS

Nordson Medical SFBP6100 sanitary fitting engineering drawing dated Jan. 10, 2012, (Year: 2012).*
(Continued)

*Primary Examiner* — Terrell L McKinnon
*Assistant Examiner* — Ding Y Tan
(74) *Attorney, Agent, or Firm* — Craig R. Miles; CR Miles P.C.

(57) ABSTRACT

Disclosed herein are embodiments of a sanitary fitting for coupling a fluid conduit to a flexible container to facilitate sterile transfer therebetween, and methods of making and using such a sanitary fitting, whereby the sanitary fitting includes a first annular member having a first annular member bore extending between first annular member first and second ends, the first annular member second end terminating in a flange radially outwardly extending therefrom, the flange comprising a substantially planar face; a second annular member having a second annular member bore extending between second annular member first and second ends, the second annular member couplable to the first annular member to axially align the first and second annular member bores to provide a first fluid flow passageway; and a valve coupled to the second annular member, the valve operable to interrupt fluid flow through a fluid flow path which includes the first fluid flow passageway.

20 Claims, 17 Drawing Sheets

(56) References Cited

U.S. PATENT DOCUMENTS

| | | | |
|---|---|---|---|
| 5,837,180 | A | 11/1998 | Linder et al. |
| 6,390,130 | B1 | 5/2002 | Guala |
| 6,607,097 | B2 | 8/2003 | Savage et al. |
| 7,544,191 | B2 | 6/2009 | Peluso et al. |
| 7,921,875 | B2* | 4/2011 | Moriiki .................. F16L 37/32 |
| | | | 137/614.04 |
| 7,950,700 | B2 | 5/2011 | Willemstyn et al. |
| 9,327,893 | B2 | 5/2016 | Steele et al. |
| 10,173,046 | B2 | 1/2019 | Ciccone et al. |
| 10,293,150 | B2 | 5/2019 | Ciccone et al. |
| 10,350,401 | B2 | 7/2019 | Ciccone et al. |
| 10,486,880 | B2 | 11/2019 | Franca et al. |
| 10,583,281 | B2 | 3/2020 | Ciccone et al. |
| 2002/0024216 | A1 | 2/2002 | Rose et al. |
| 2002/0093192 | A1* | 7/2002 | Matkovich ............. F16L 37/38 |
| | | | 285/915 |
| 2007/0160785 | A1* | 7/2007 | Hsu ........................ B32B 27/08 |
| | | | 428/35.2 |
| 2009/0051161 | A1 | 2/2009 | Ekstrom |
| 2012/0228873 | A1* | 9/2012 | Steele ................ B65D 75/5877 |
| | | | 285/399 |
| 2013/0245531 | A1 | 9/2013 | Brandl et al. |
| 2017/0080139 | A1 | 3/2017 | Gossmann et al. |
| 2017/0205011 | A1* | 7/2017 | Ciccone ............. A61M 39/1011 |
| 2018/0304066 | A1 | 10/2018 | Ciccone et al. |
| 2019/0078714 | A1 | 3/2019 | Brugger et al. |
| 2019/0105122 | A1 | 4/2019 | Miller et al. |
| 2019/0269901 | A1 | 9/2019 | Ciccone et al. |
| 2020/0188651 | A1 | 6/2020 | Ciccone et al. |

OTHER PUBLICATIONS

Nordson Medical value plastic bioprocessing components catalog for 2015 (Year: 2015).*

PCT International Patent Application No. PCT/US21/39874, International Search Report and Written Opinion of the International Searching Authority dated Oct. 7, 2021, 14 pages.

Nordson Medical. Shop Fluid Management Products. Website, https://www.nordsonmedical.com; originally Downloaded Jun. 29, 2020, 3 pages.

PCT International Patent Application No. PCT/US22/35669, International Search Report and Written Opinion of the International Searching Authority dated Oct. 20, 2022, 11 pages.

* cited by examiner

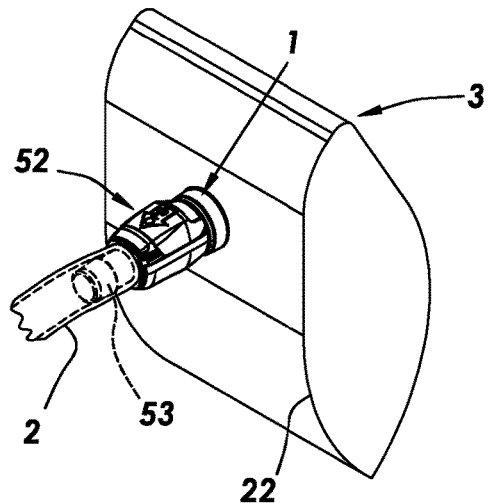
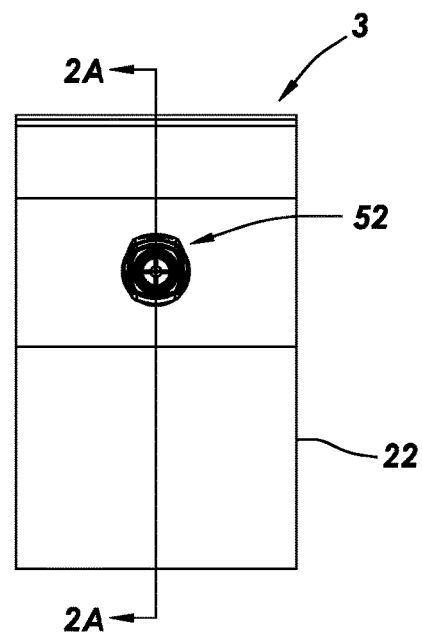
FIG.1A
FIG.1B
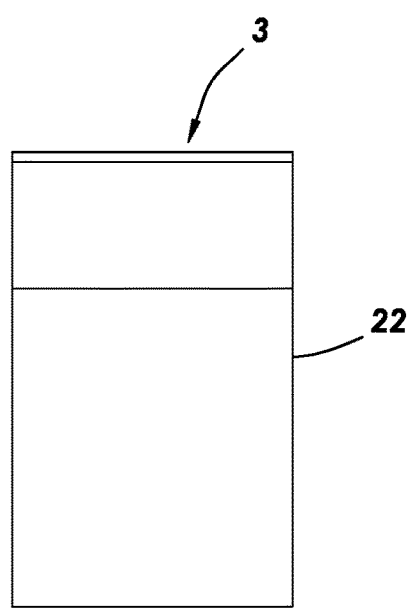
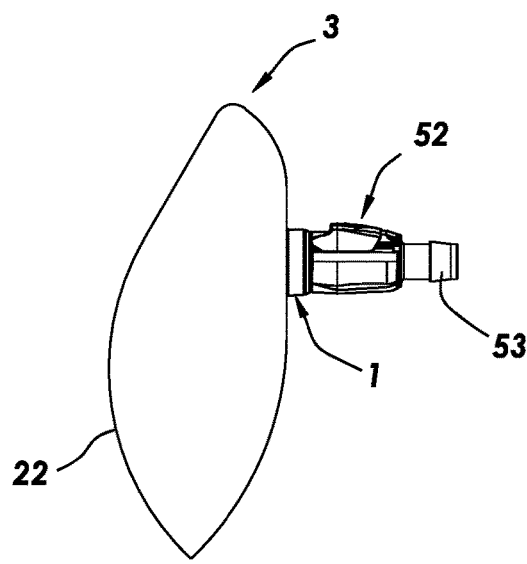
FIG.1C
FIG.1D

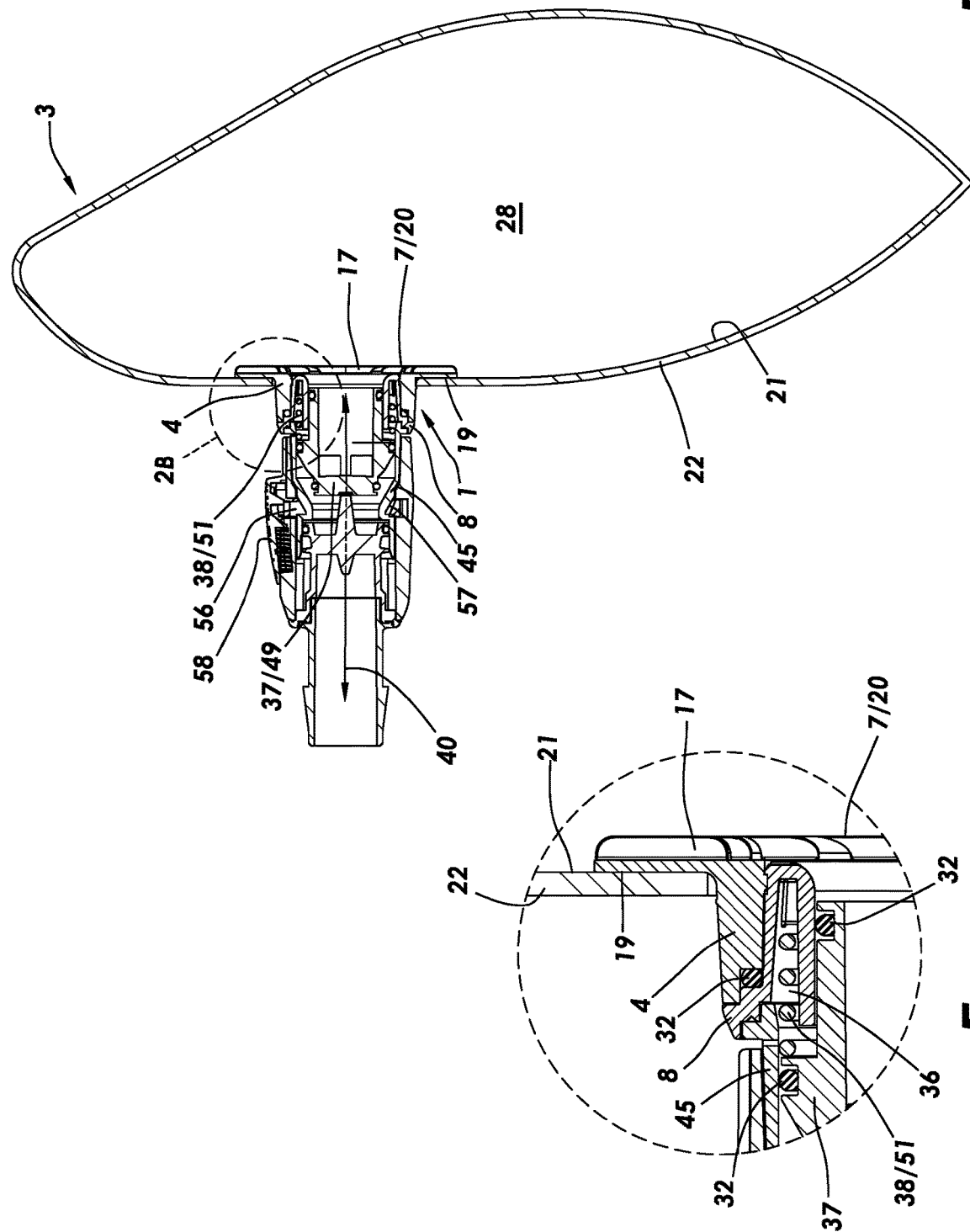

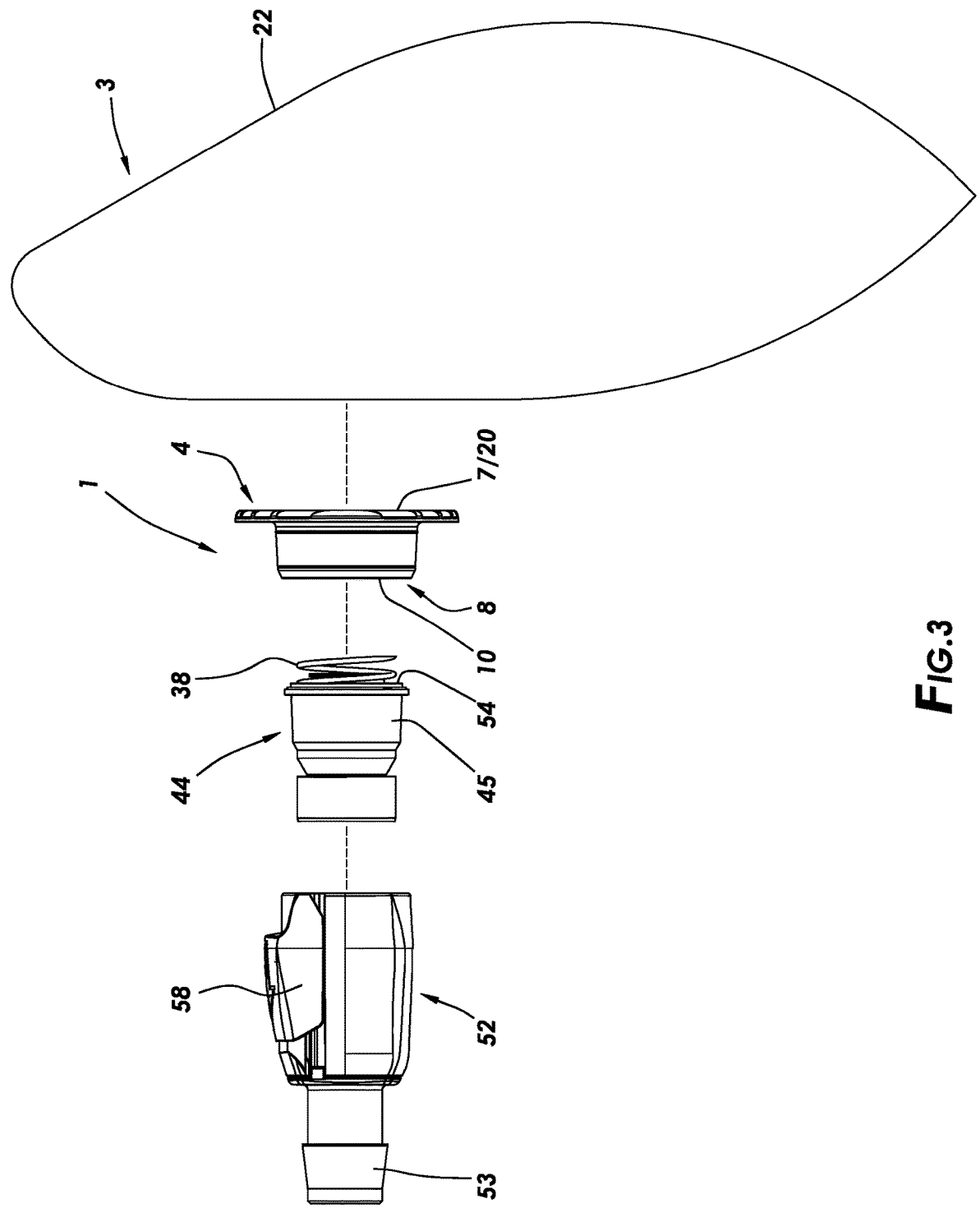

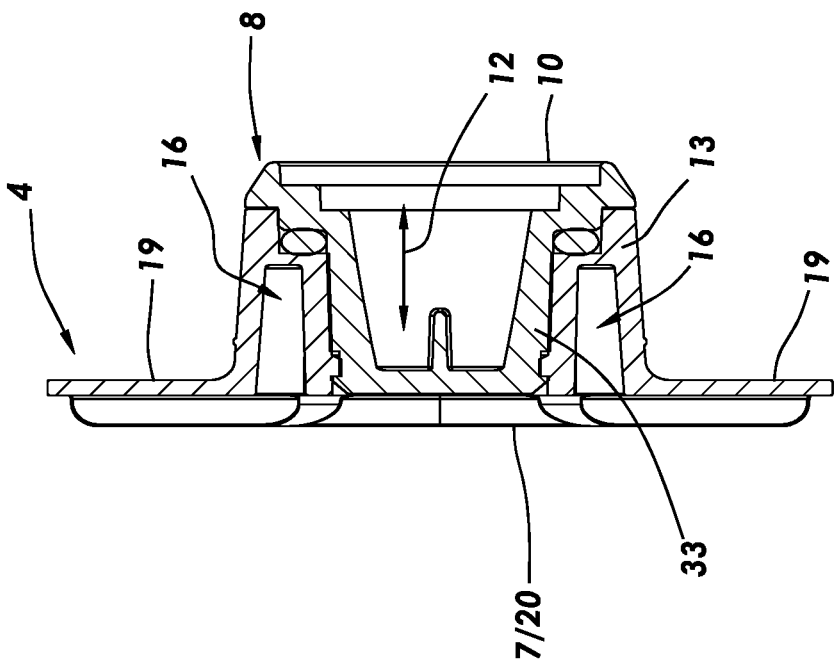
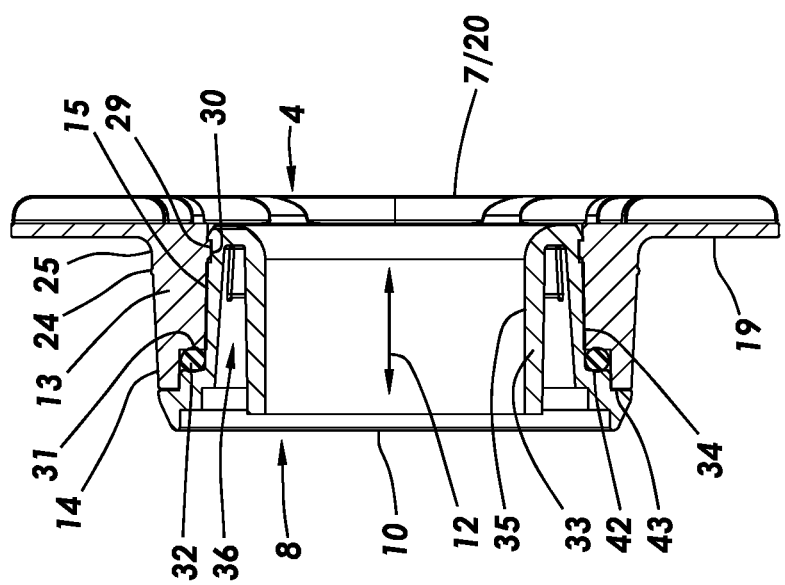

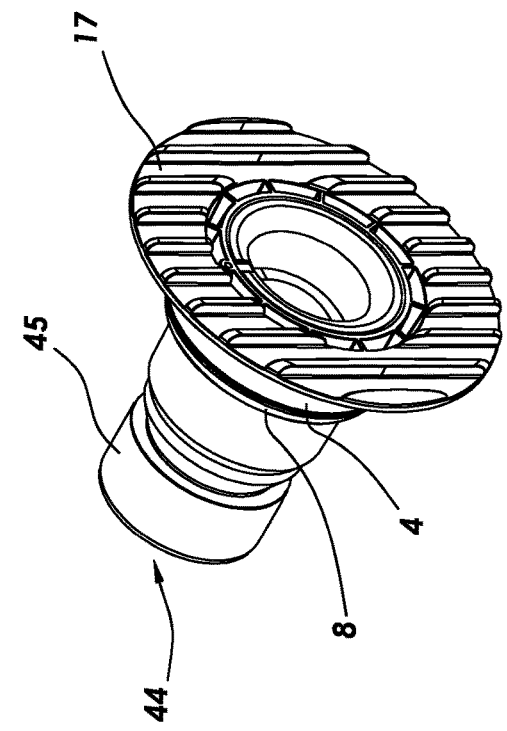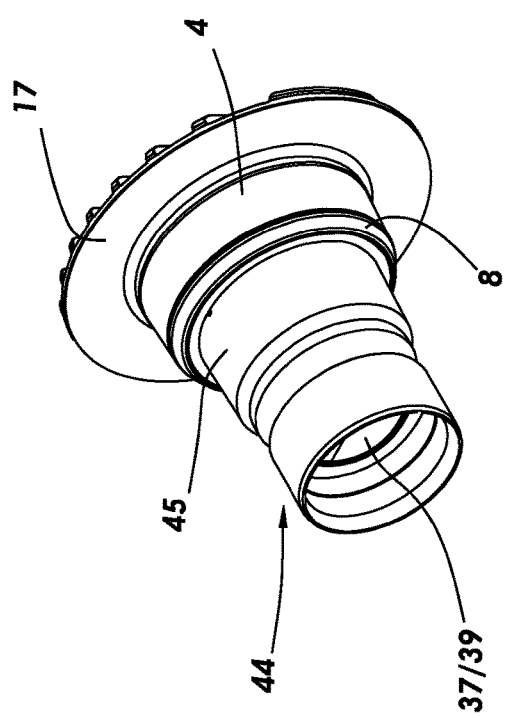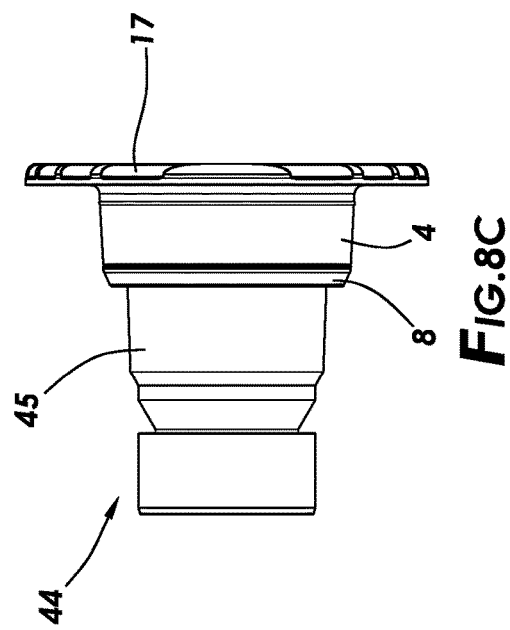

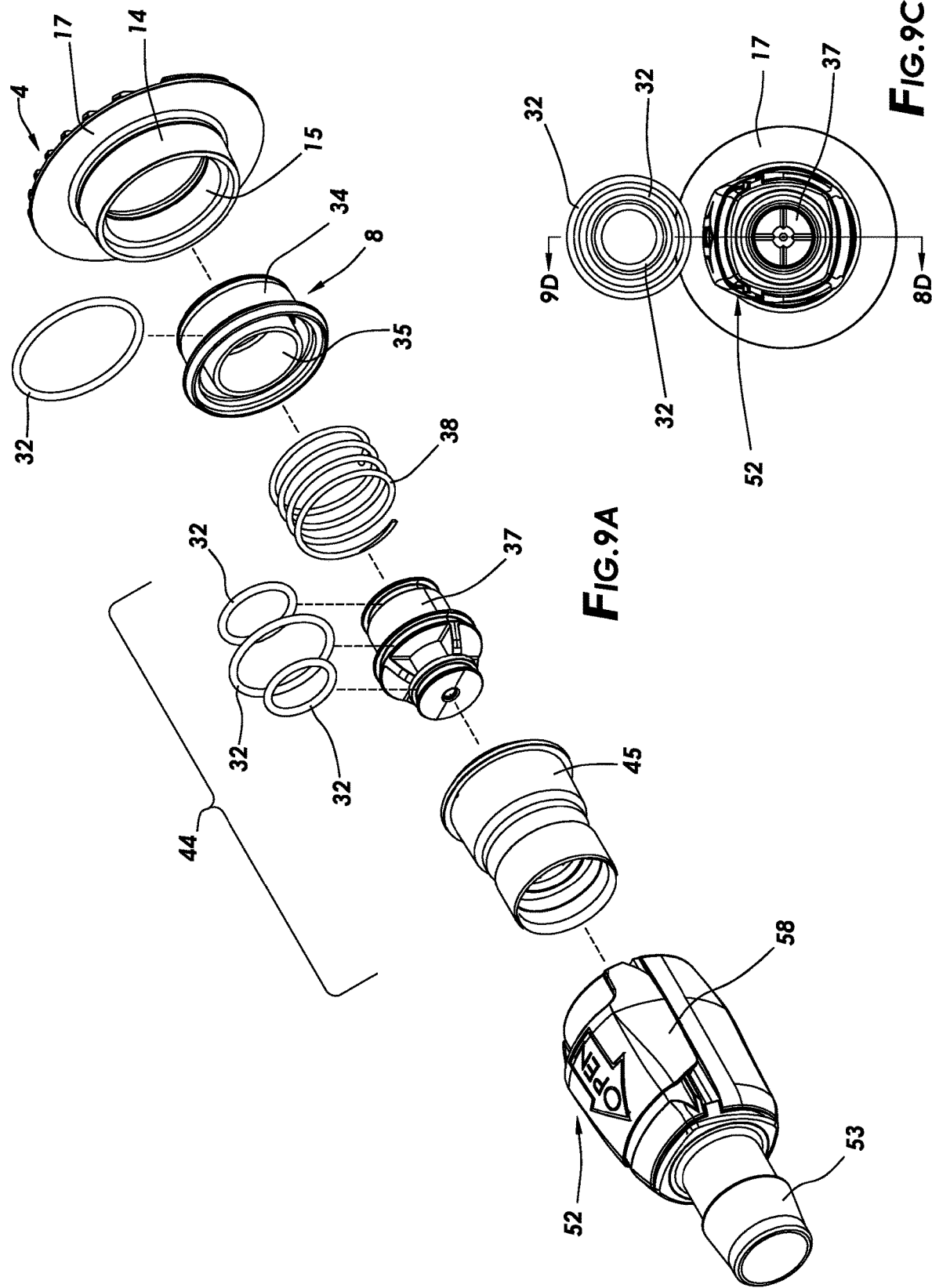

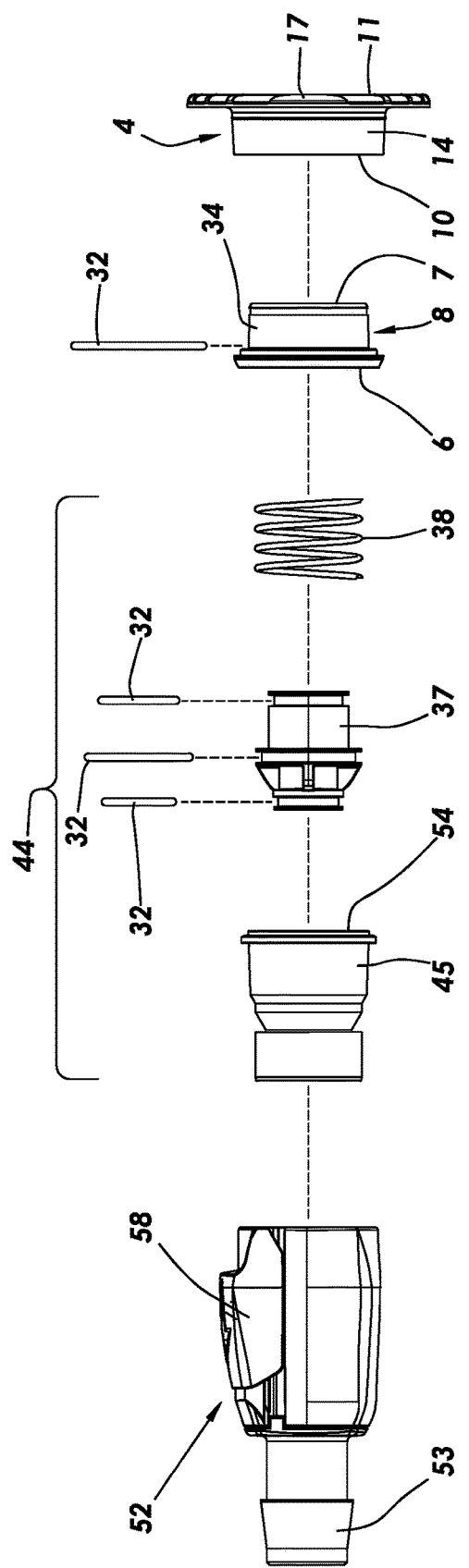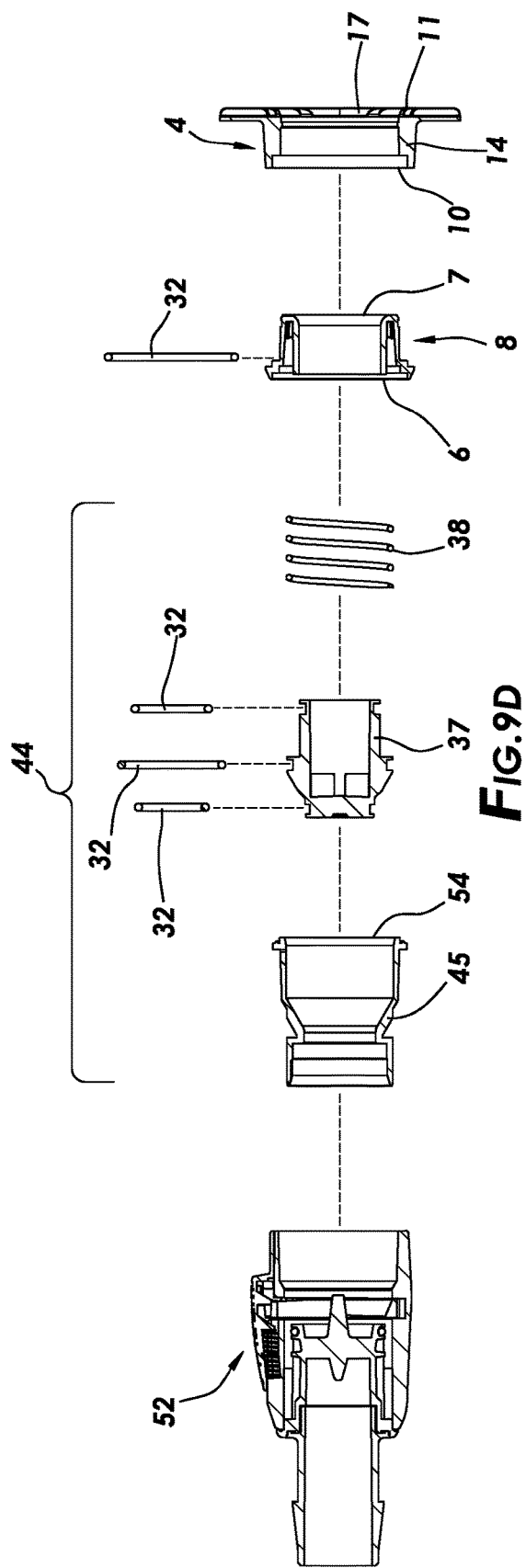

SANITARY FITTING

I. SUMMARY OF THE INVENTION

A broad object of a particular embodiment of the invention can be to provide a sanitary fitting which may be useful for coupling a fluid conduit to a flexible container to facilitate sterile transfer of fluid therebetween, and methods of making and using such a sanitary fitting, whereby the sanitary fitting includes a first annular member having a first annular member bore extending between first annular member first and second ends, the first annular member second end terminating in a flange radially outwardly extending therefrom, the flange comprising a substantially planar face; a second annular member having a second annular member bore extending between second annular member first and second ends, the second annular member couplable to the first annular member to axially align the first and second annular member bores to provide a first fluid flow passageway; and a valve coupled to the second annular member, the valve operable to interrupt fluid flow through a fluid flow path which includes the first fluid flow passageway.

Naturally, further objects of the invention are disclosed throughout other areas of the specification, drawings, and claims.

II. A BRIEF DESCRIPTION OF THE DRAWINGS

FIG. 1A shows a perspective view of a method of using a particular embodiment of a sanitary fitting in conjunction with a fluid conduit and a bag.

FIG. 1B shows a front view of a particular embodiment of a sanitary fitting in conjunction with a bag.

FIG. 1C shows a rear view of the particular embodiment of the sanitary fitting in conjunction with the bag shown in FIG. 1B.

FIG. 1D shows a first side view of the particular embodiment of the sanitary fitting in conjunction with the bag shown in FIG. 1B.

FIG. 2A shows a cross-sectional view of the particular embodiment of the sanitary fitting in conjunction with the bag shown in FIG. 1B.

FIG. 2B shows an enlarged view of a portion of the particular embodiment of the sanitary fitting in conjunction with the bag shown in FIG. 2A.

FIG. 3 shows an exploded view of the particular embodiment of the sanitary fitting in conjunction with the bag shown in FIG. 1E.

FIG. 4I shows a cross-sectional view of the particular embodiment of the sanitary fitting shown in FIG. 4C.

FIG. 4J shows a cross-sectional view of the particular embodiment of the sanitary fitting shown in FIG. 4D.

FIG. 8A shows a perspective view of a particular embodiment of a sanitary fitting including a first annular member, a second annular member, and a valve assembly.

FIG. 8B shows another perspective view of the particular embodiment of the sanitary fitting shown in FIG. 8A.

FIG. 8C shows a side view of the particular embodiment of the sanitary fitting shown in FIG. 8A.

FIG. 9A shows an exploded perspective view of a particular embodiment of a sanitary fitting including a first annular member, a second annular member, and a valve assembly.

FIG. 9B shows a side view of the particular embodiment of the sanitary fitting shown in FIG. 9A.

FIG. 9C shows a front view of the particular embodiment of the sanitary fitting shown in FIG. 9A.

FIG. 9D shows a cross-sectional view of the particular embodiment of the sanitary fitting shown in FIG. 9C.

III. DETAILED DESCRIPTION OF THE PREFERRED EMBODIMENTS

Figure 1E:
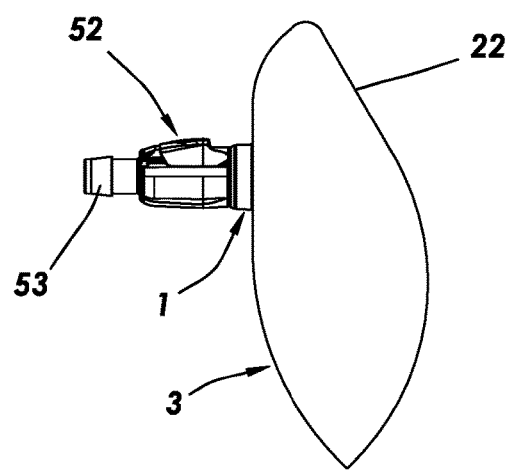
FIG. 1E shows a second side view of the particular embodiment of the sanitary fitting in conjunction with the bag shown in FIG. 1B.
Figure 1F:
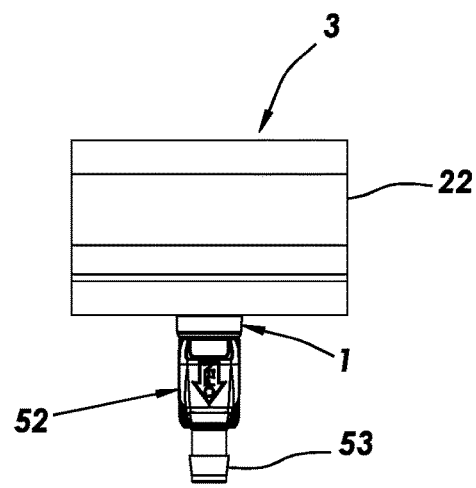
FIG. 1F shows a top view of the particular embodiment of the sanitary fitting in conjunction with the bag shown in FIG. 1B.
Figure 1G:
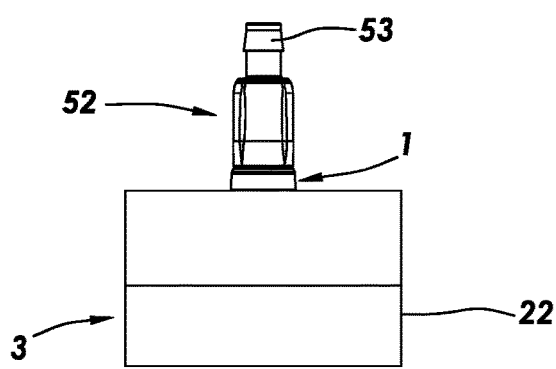
FIG. 1G shows a bottom view of the particular embodiment of the sanitary fitting in conjunction with the bag shown in FIG. 1B.

Now referring primarily to FIGS. 1A through 3, which illustrate a method of using a particular embodiment of the inventive sanitary fitting (1) for releasably connecting together a fluid conduit (2) (such as tubing, for example medical tubing) with a flexible container (3) (such as a bag, for example a "single-use" bag) to facilitate sterile transfer of fluid therebetween, such as for a biomedical application. Advantageously, the sanitary fitting (1) can be relatively easily and securely connected to the fluid conduit (2), and yet relatively easily intentionally disconnected.

Now referring primarily to FIG. 4A through FIG. 5D, and FIGS. 8A through 9D, the sanitary fitting (1) includes (i) a first annular member (4) having a first annular member bore (5) extending between first annular member first and second ends (6)(7), and (ii) a second annular member (8) having a second annular member bore (9) extending between second annular member first and second ends (10)(11). The second annular member (8) can be couplable/connectable to the first annular member (4) to axially align the first and second annular member bores (5)(9) to provide a first fluid flow passageway (12).

First Annular Member

Figure 5A:
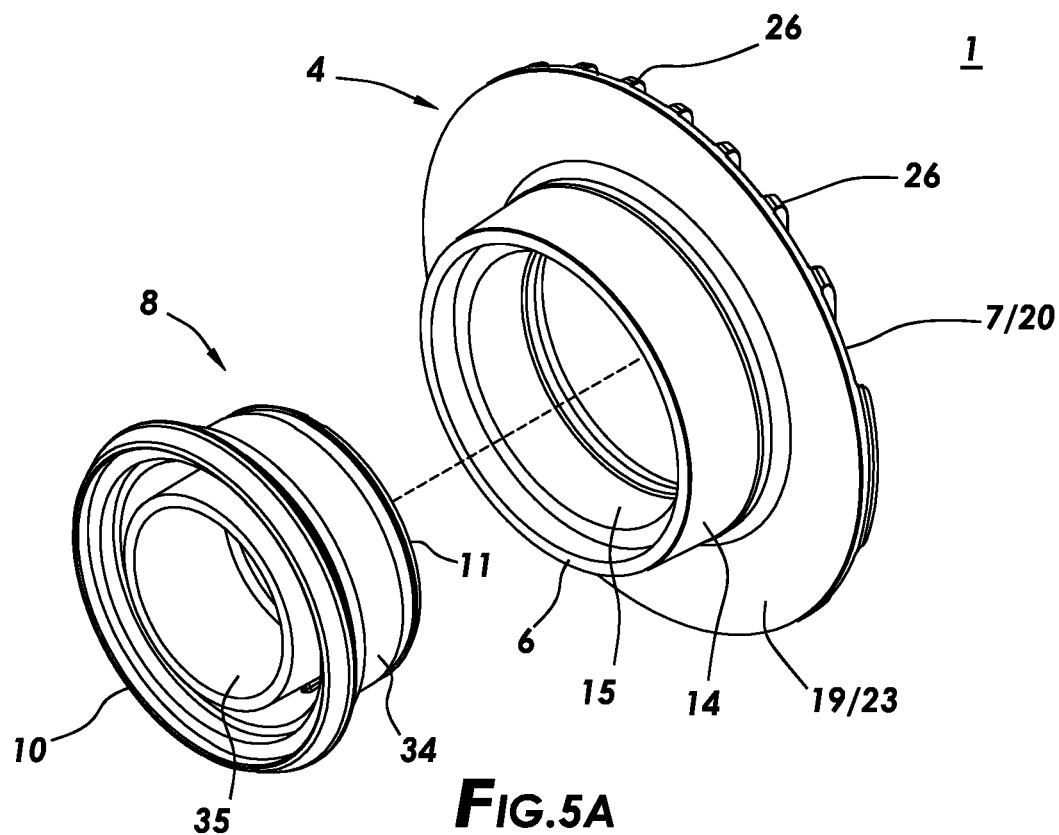
FIG. 5A shows an exploded perspective view of a particular embodiment of the sanitary fitting including first and second annular members.
Figure 5B:
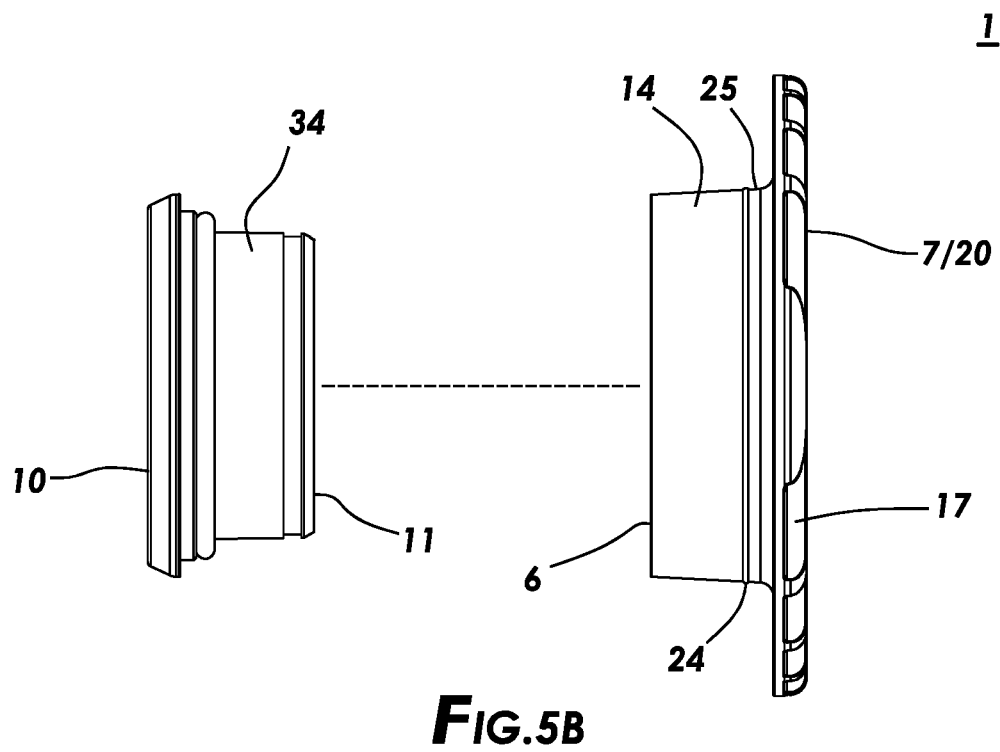
FIG. 5B shows a side view of the particular embodiment of the sanitary fitting shown in FIG. 5A.
Figure 5C:
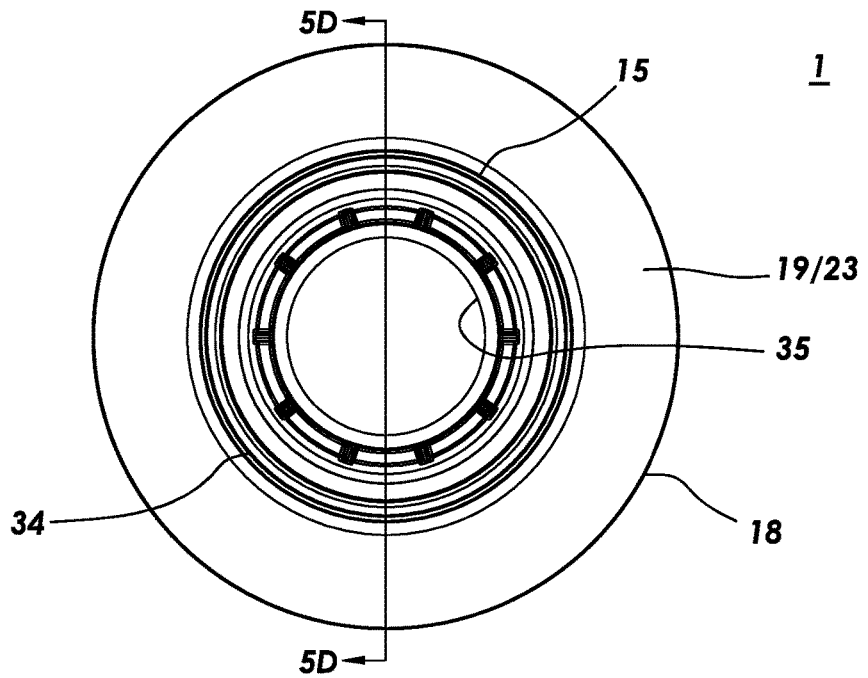
FIG. 5C shows a front view of the particular embodiment of the sanitary fitting shown in FIG. 5A.
Figure 5D:
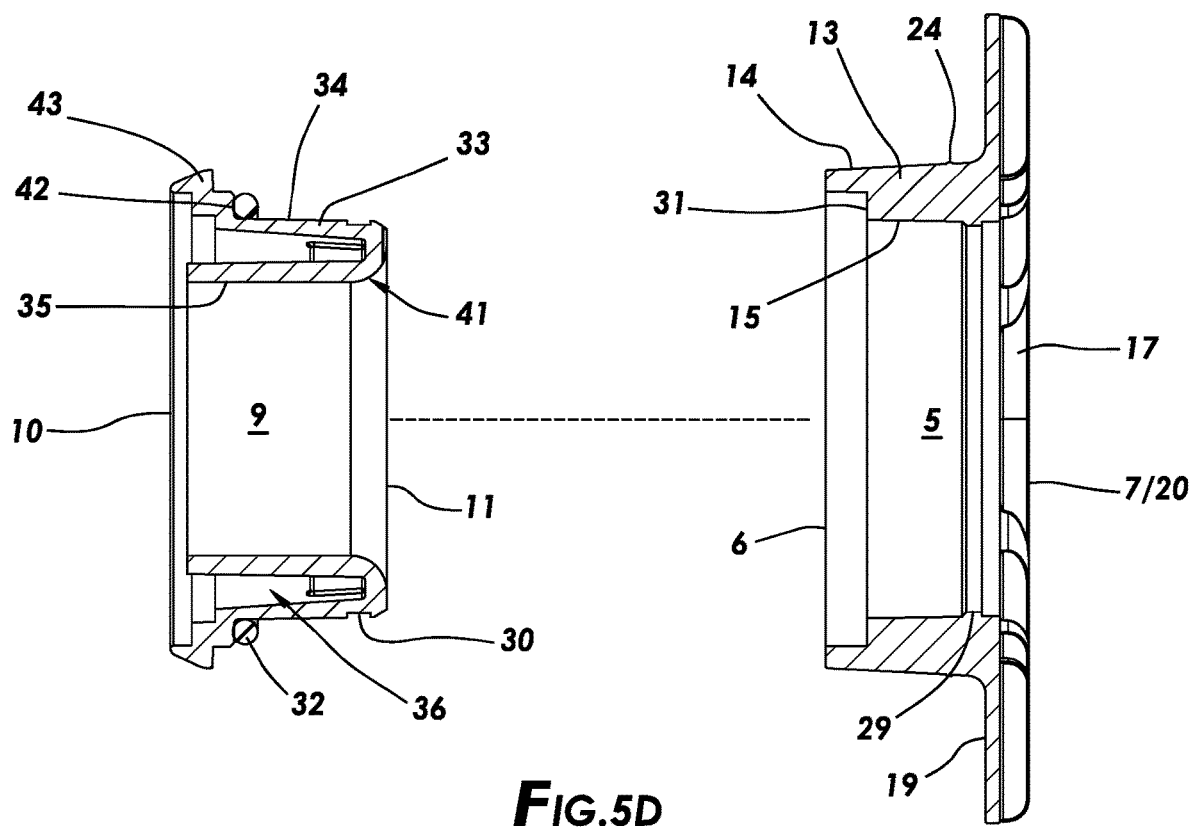
FIG. 5D shows a cross-sectional view of the particular embodiment of the sanitary fitting shown in FIG. 5C.
Figure 6B:
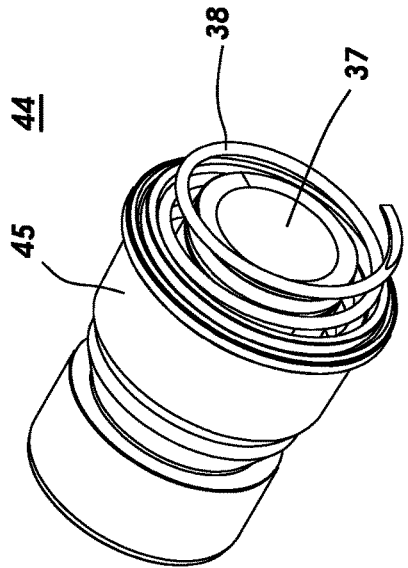
FIG. 6B shows another perspective view of the particular embodiment of the valve assembly shown in FIG. 6A.
Figure 6D:
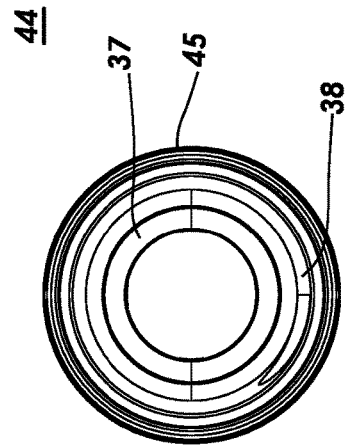
FIG. 6D shows a rear view of the particular embodiment of the valve assembly shown in FIG. 6A.
Figure 6A:
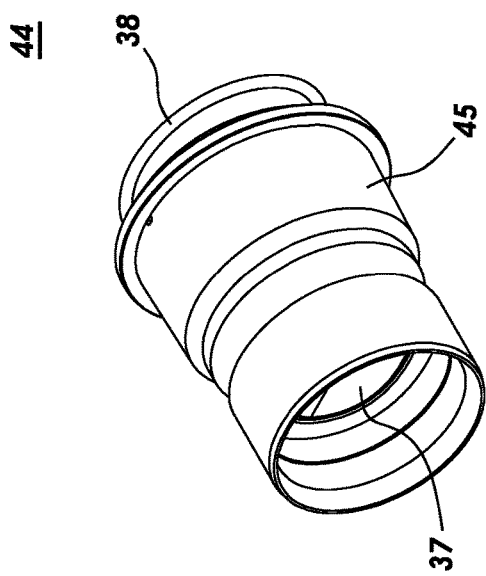
FIG. 6A shows a perspective view of a particular embodiment of a valve assembly of the sanitary fitting, the valve assembly including a sleeve and a valve movable within the sleeve.
Figure 6C:
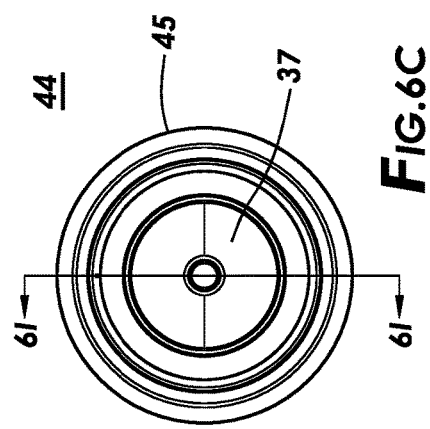
FIG. 6C shows a front view of the particular embodiment of the valve assembly shown in FIG. 6A.
Figure 6E:
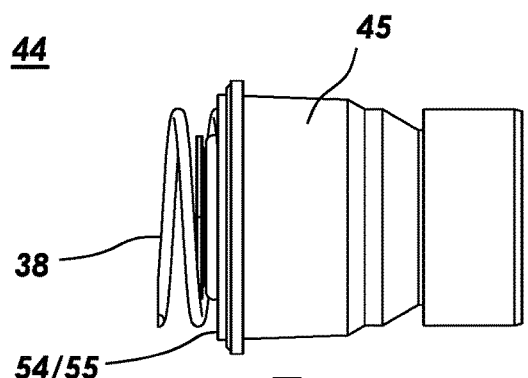
FIG. 6E shows a first side view of the particular embodiment of the valve assembly shown in FIG. 6A.
Figure 6F:
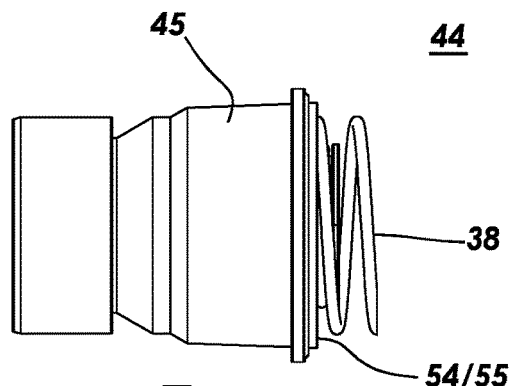
FIG. 6F shows a second side view of the particular embodiment of the valve assembly shown in FIG. 6A.
Figure 6G:
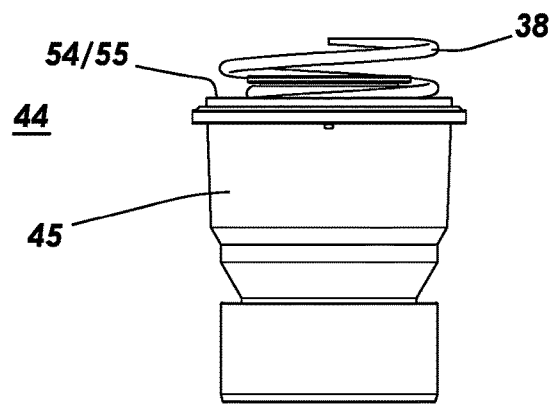
FIG. 6G shows a top view of the particular embodiment of the valve assembly shown in FIG. 6A.
Figure 6H:
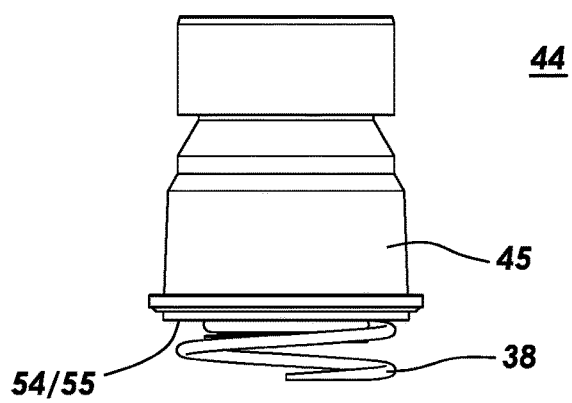
FIG. 6H shows a bottom view of the particular embodiment of the valve assembly shown in FIG. 6A.
Figure 6I:
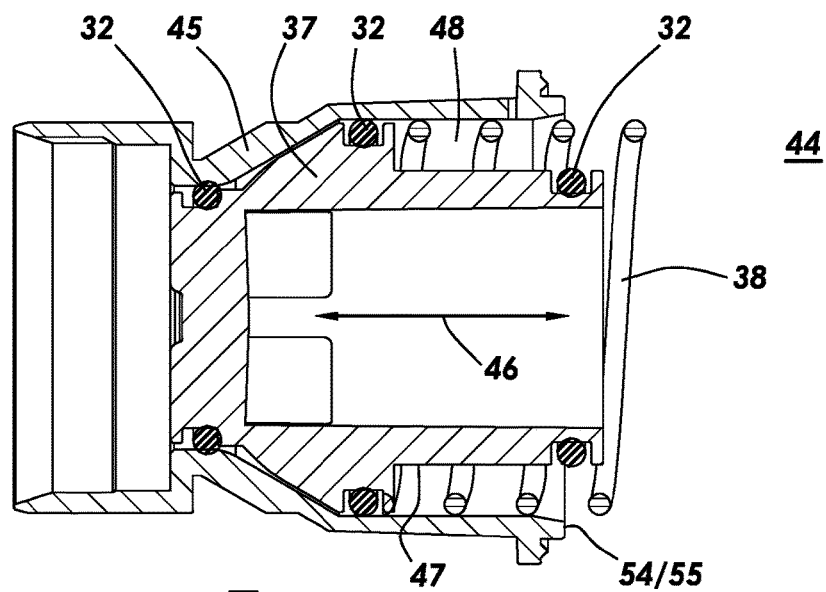
FIG. 6I shows a cross-sectional view of the particular embodiment of the valve assembly shown in FIG. 6C.
Figure 7A:
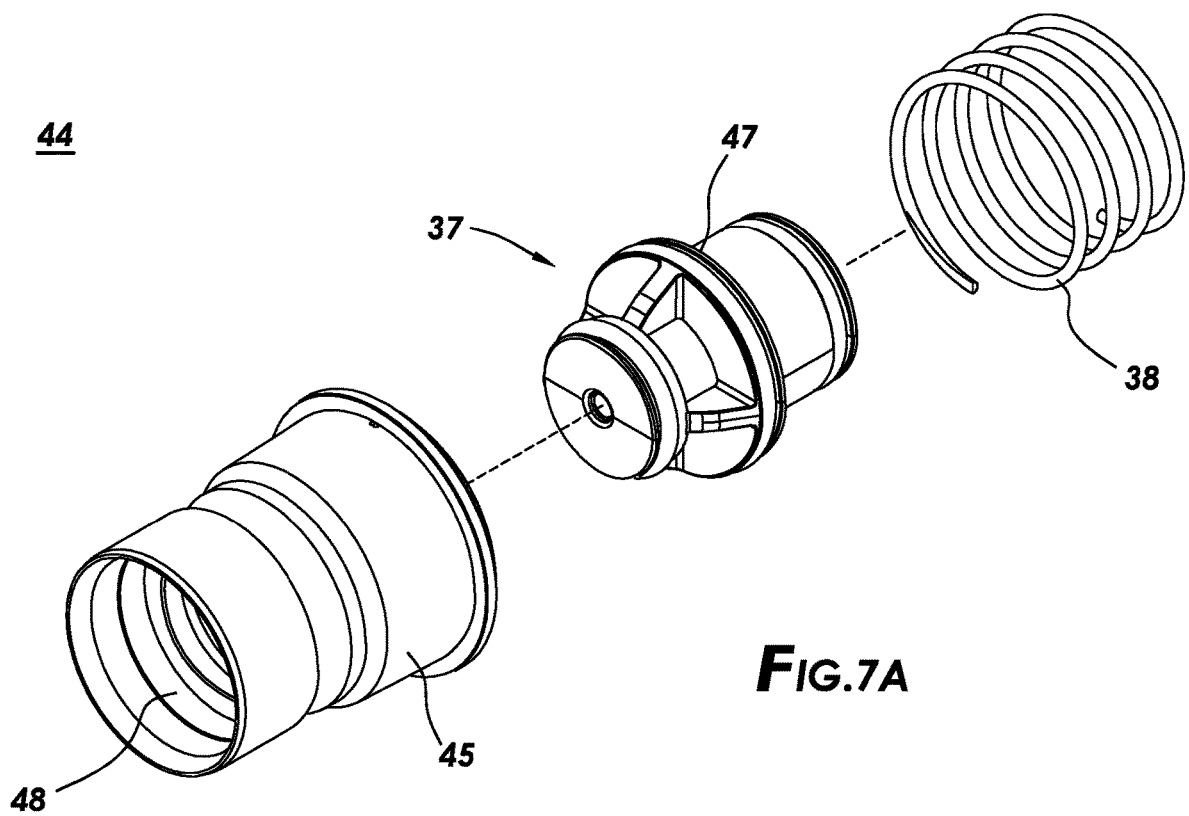
FIG. 7A shows an exploded perspective view of a particular embodiment of a valve assembly of the sanitary fitting, the valve assembly including a sleeve, a valve movable within the sleeve, and a valve-biasing member.
Figure 7B:
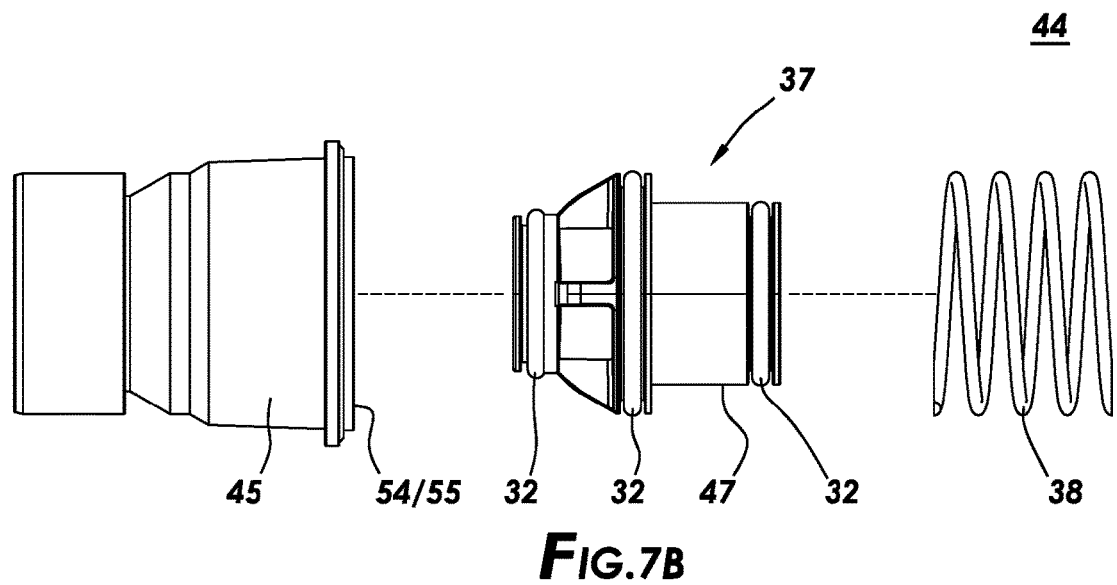
FIG. 7B shows a side view of the particular embodiment of the valve assembly shown in FIG. 7A.
Figure 7C:
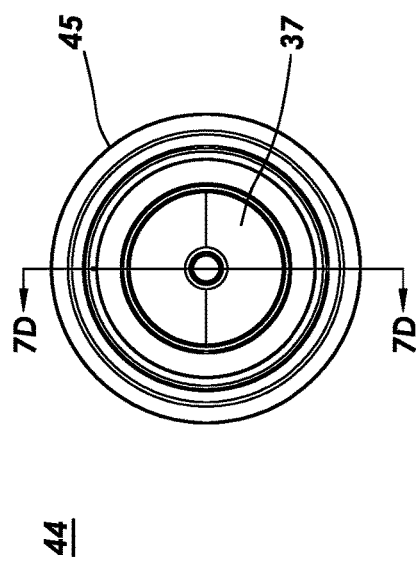
FIG. 7C shows a front view of the particular embodiment of the valve assembly shown in FIG. 7A.
Figure 7D:
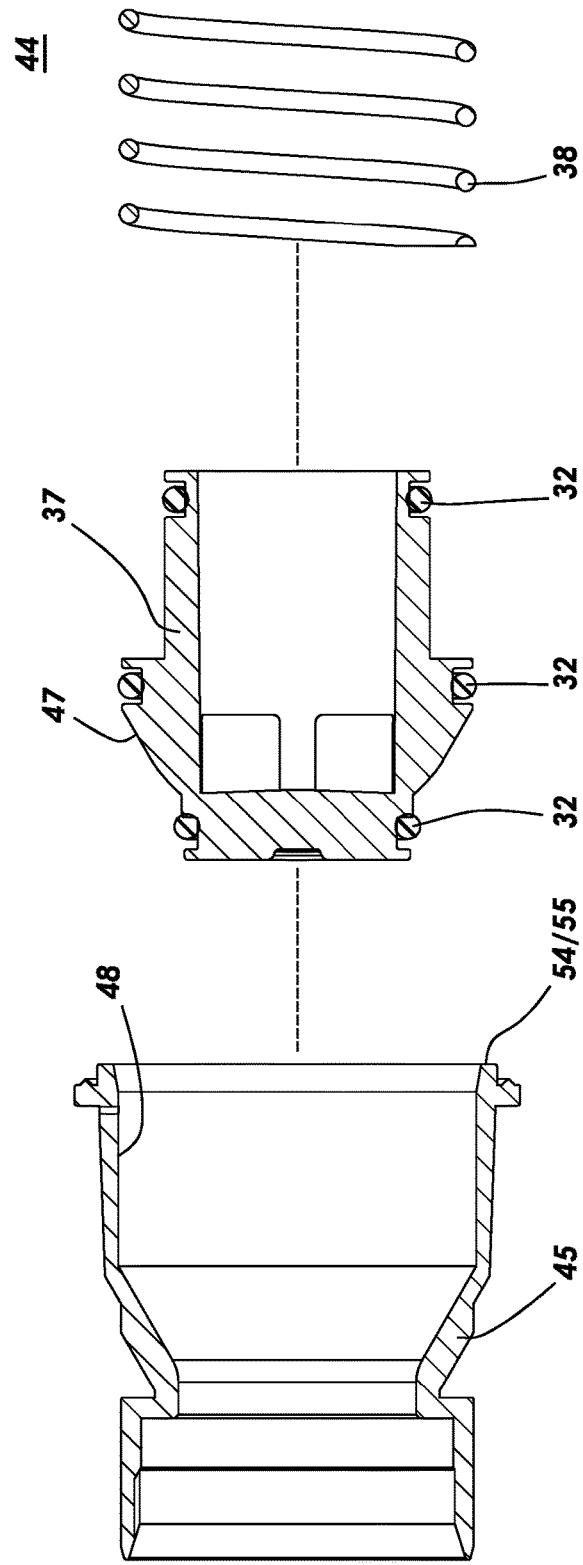
FIG. 7D shows a cross-sectional view of the particular embodiment of the valve assembly shown in FIG. 7C.

With reference to FIG. 5D in particular, the first annular member (4) includes a first annular member wall (13) having opposing first annular member wall outer and inner surfaces (14)(15), whereby the first annular member wall inner surface (15) defines the first annular member bore (5). As to particular embodiments, the first annular member wall (13) may be substantially cylindrical or cylindrical and correspondingly, may have a substantially circular or circular cross section; thus, the first annular member wall inner surface (15) may define a first annular member bore (5) having a substantially circular or circular cross section. However, it is also herein contemplated that the first annular member wall (13) may define any shape or configuration useful for connecting the sanitary fitting (1) to a bag (3) for the transfer of fluid via the sanitary fitting (1) between a fluid conduit (2) and the bag (3).

As can be seen in FIG. 4J, as to particular embodiments, the first annular member wall (13) can include a plurality of elongate openings (16) extending axially inward from the first annular member second end (7), whereby the elongate openings (16) can dispose in circumferentially spaced-apart relation, and may be useful for manufacturing of the first annular member (4), particularly by an injection molding process.

The first annular member (4) further includes a flange (17) (or projecting edge or rim) radially outwardly extending from the first annular member second end (7) or, said another way, the first annular member second end (7) can terminate in a flange (17) radially outwardly extending therefrom. As to particular embodiments, the flange (17) can outwardly extend from the first annular member second end (7) in only a radially outward direction or, said another way, in a direction consisting of radially outward; correspondingly, as to this embodiment, the flange (17) does not extend axially outward from the first annular member second end (7).

The flange (17) can be defined by a flange outer edge (18) which connects opposing flange first and second faces (19)(20), whereby the flange first face (19) can dispose toward or face the first annular member first end (6) and the flange second face (20) can provide the first annular member second end (7). As to particular embodiments, the flange (17) can have a substantially circular or circular cross section, and can be concentric with the first annular member wall (13) and the first annular member bore (5).

The flange first face (19) can be substantially planar or planar. As to particular embodiments, the entirety of the flange first face (19), meaning the entire surface area of the flange first face (19) between the first annular member wall outer surface (14) and the flange outer edge (18), can be substantially planar or planar, thereby providing a sufficient amount of surface area to facilitate engagement of the flange first face (19) with a bag wall interior surface (21) of the bag (3) to couple, connect, or directly connect the first annular member (4) to the bag (3).

In use, the first annular member (4) can couple to a bag (3) to facilitate sterile transfer of fluid between a fluid conduit (2) and the bag (3), whereby the flange first face (19) can be hermetically sealed to the bag wall interior surface (21), for example via a welding process. Following, for such a coupling, the flange first face (19) can be disposed proximate the bag wall interior surface (21), and a welder can provide heat (typically) to weld the flange first face (19) to the bag wall (22). This weld can be impermeable, which can maintain sterility within the bag (3). Once the sanitary fitting (1) is coupled to the bag (3), fluid can be transferred through the sanitary fitting (1), either into or out of the bag (3), while maintaining this sterility.

To facilitate welding, the flange first face (19) can be formed from a first material (23), typically a polymeric material, preselected based on its weldability to the bag wall (22). As but illustrative, non-limiting examples, the first material (23) can be polyethylene, polypropylene, polyolefin, or a thermoplastic elastomer, which may be useful for welding to a bag wall (22) formed from polypropylene.

Now referring primarily to FIGS. 4E through 4I, as to particular embodiments, the first annular member (4) can further include an annular lip (24) radially outwardly extending from the first annular member wall outer surface (14) proximate the flange first face (19) and in axially spaced-apart relation to the flange first face (19), whereby the first annular member wall outer surface portion (25) which disposes between the flange first face (19) and the annular lip (24) can provide an engagement surface for the bag wall (22), thereby facilitating the coupling of the bag (3) to the first annular member (4). Accordingly, the annular lip (24) can be disposed a distance of about a thickness of the bag wall (22) or a little greater than the thickness of the bag wall (22) from the flange first face (19) in the axial direction.

As to particular embodiments, the flange second face (20) can be substantially planar or planar. As to particular embodiments, the entirety of the flange second face (20), meaning the entire surface area of the flange second face (20) between (i) the first annular member wall outer surface (14) and/or the first annular member wall inner surface (15) and (ii) the flange outer edge (18), can be substantially planar or planar. As to these embodiments, the flange first and second faces (19)(20) can dispose in spaced-apart, substantially parallel relation or parallel relation.

Now referring primarily to FIGS. 4A, 4B, 4D, 4G, and 4H, as to particular embodiments, one or more protrusions (26) can axially outwardly extend from the flange second face (20). As to particular embodiments, a protrusion (26) may protrude generally normally to the flange second face (20).

Figure 4B:
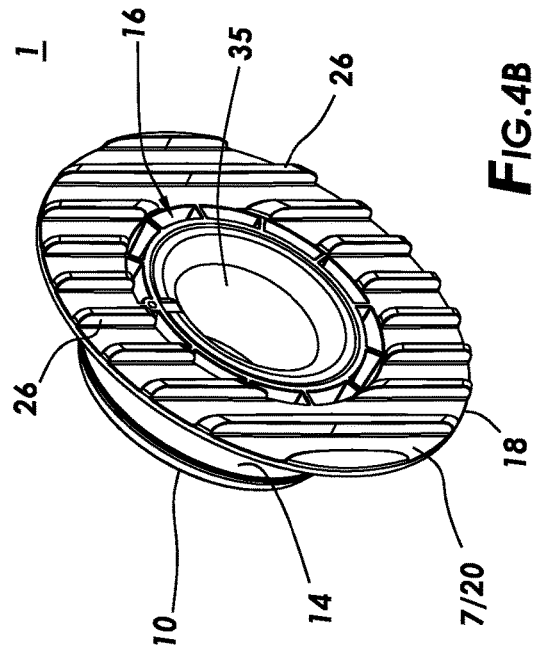
FIG. 4B shows another perspective view of the particular embodiment of the sanitary fitting shown in FIG. 4A.
Figure 4D:
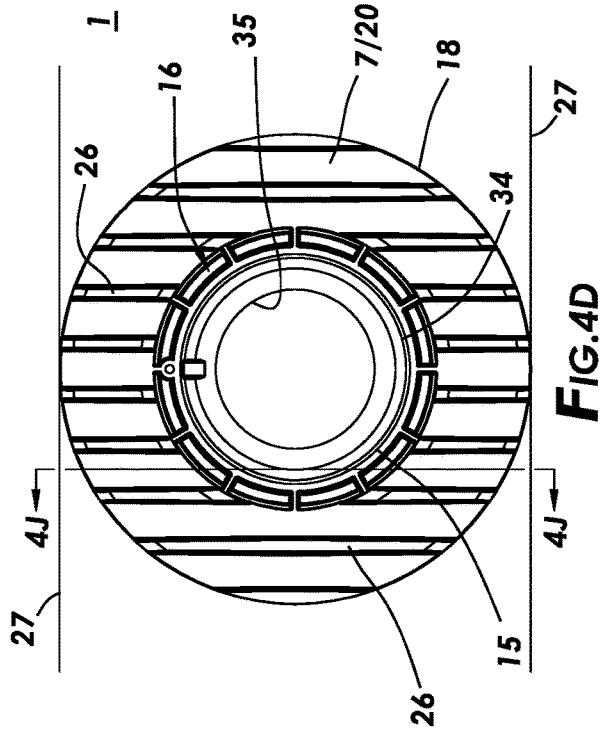
FIG. 4D shows a rear view of the particular embodiment of the sanitary fitting shown in FIG. 4A.
Figure 4A:
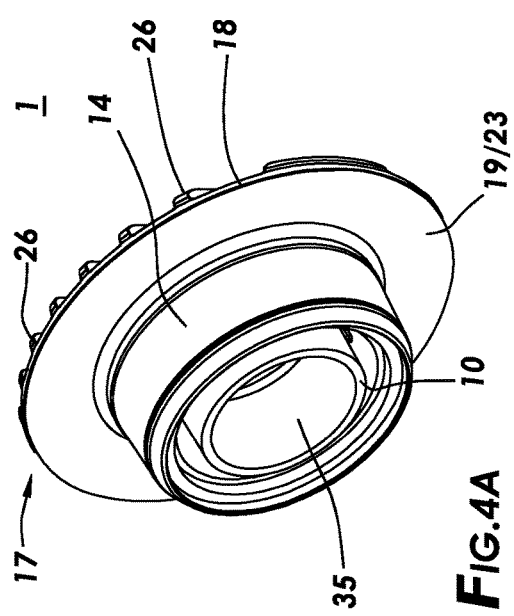
FIG. 4A shows a perspective view of a particular embodiment of the sanitary fitting including first and second annular members.
Figure 4C:
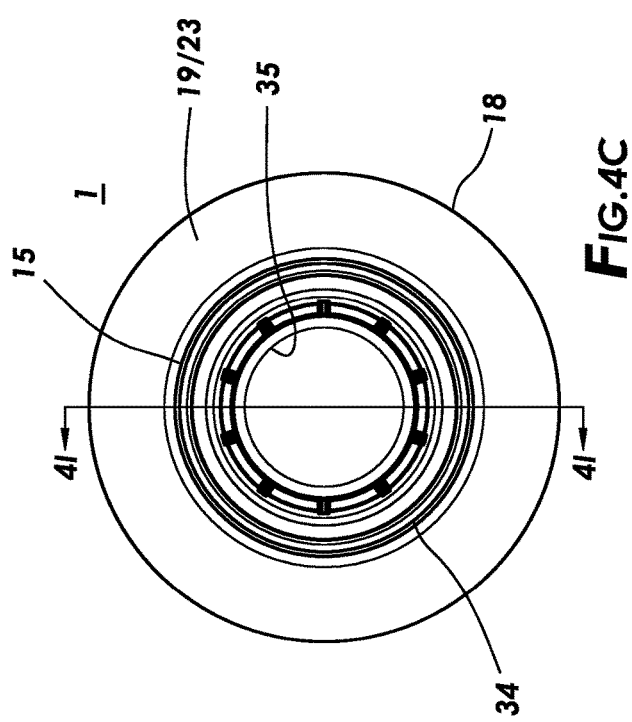
FIG. 4C shows a front view of the particular embodiment of the sanitary fitting shown in FIG. 4A.
Figure 4F:
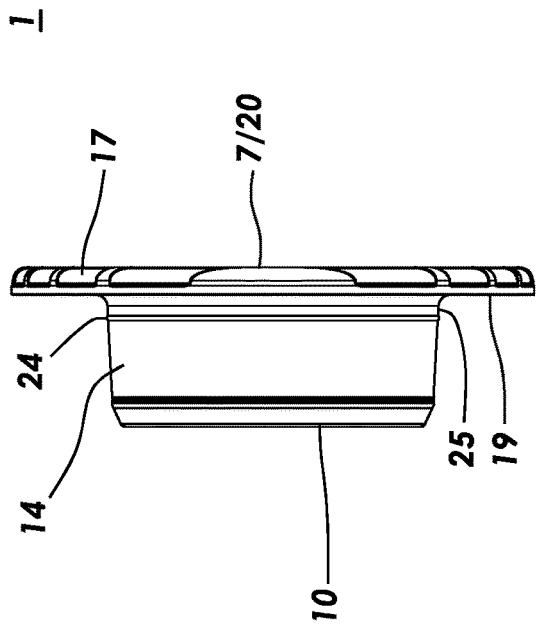
FIG. 4F shows a second side view of the particular embodiment of the sanitary fitting shown in FIG. 4A.
Figure 4H:
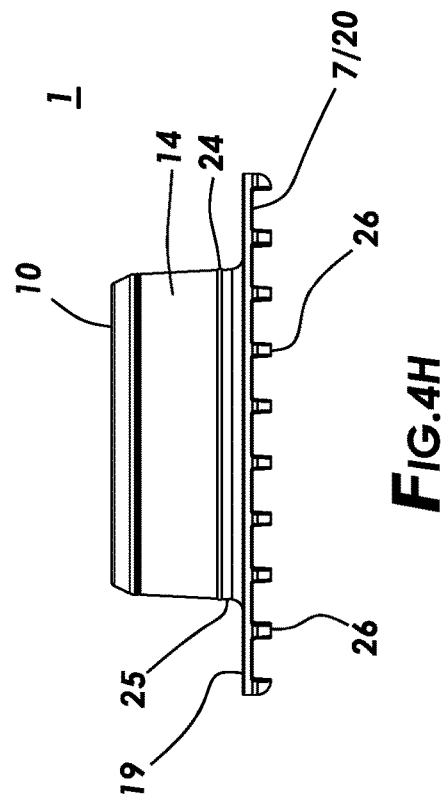
FIG. 4H shows a bottom view of the particular embodiment of the sanitary fitting shown in FIG. 4A.
Figure 4E:
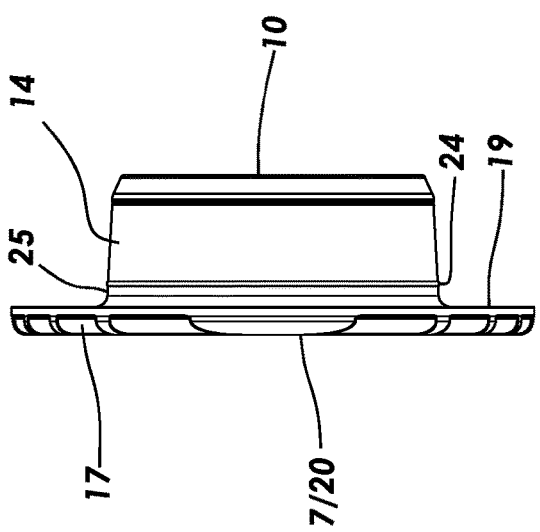
FIG. 4E shows a first side view of the particular embodiment of the sanitary fitting shown in FIG. 4A.
Figure 4G:
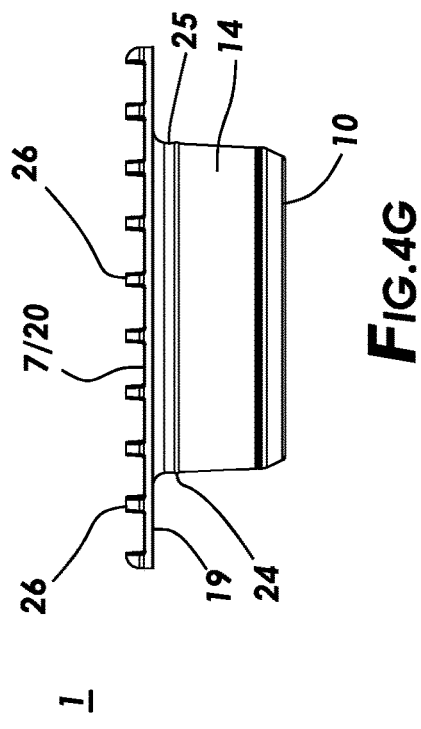
FIG. 4G shows a top view of the particular embodiment of the sanitary fitting shown in FIG. 4A.

As to particular embodiments, a protrusion (26) can be configured as a linear protrusion (26), whereby linear can mean extending along a straight line. Notably, a linear protrusion (26) can be in contrast to a protrusion having a curve, arc, or twisting curvature. As to particular embodiments, the linear protrusion (26) can have a length extending between opposing ends (27) of the flange outer edge (18) (as shown in FIG. 4D), which may be distinguished from a protrusion which radially outwardly extends from a central bore.

As to particular embodiments, a plurality of linear protrusions (26) can axially outwardly extend from the flange second face (20) and dispose in spaced-spaced, substantially parallel relation or parallel relation, whereby these protrusions (26) may function to space the bag wall (22) from the portion of the first annular member bore (5) which passes through the flange (17). Correspondingly, the protrusions (26) may prevent the bag wall (22) from engaging with the flange second face (20) proximate the first annular member bore (5), as such an engagement may act to seal the portion of the first annular member bore (5) which passes through the flange (17), thus precluding fluid flow between the fluid conduit (2) and a bag interior space (28) of the bag (3). For example, even if the bag wall (22) is forcibly urged into the first annular member bore (5) proximate the flange (17), fluid can continue to flow between the bag (3) and the sanitary fitting (1) via the channels formed between the protrusions (26).

Now referring primarily to FIG. 5D, the first annular member wall (13) can further include a tongue (29), such as an annular tongue (29), radially outwardly extending from the first annular member wall inner surface (15) into the first annular member bore (9), whereby the tongue (29) can be configured for reception within a mating groove (30), such as an annular groove (30), of the second annular member (8) upon coupling of the first and second annular members (4)(8). Of course, the reverse is also herein contemplated, such that a groove can radially inwardly extend into the first annular member wall inner surface (15) and accordingly, the second annular member (8) can include the mating tongue.

Now referring primarily to FIGS. 4I and 5D, the first annular member wall inner surface (15) can include a first annular member shoulder (31), which may be configured to receive or seat a seal (32), such as an annular seal (for example, an o-ring), upon coupling of the first and second annular members (4)(8), whereby the seal (32) can function to sealably engage the first and second annular members (4)(8).

Second Annular Member

Now referring primarily to FIG. 4A through FIG. 5D, and FIGS. 8A through 9D, the sanitary fitting (1) further includes a second annular member (8) having a second annular member bore (9) extending between second annular member first and second ends (10)(11), whereby the second annular member (8) can be couplable to the first annular member (4) to axially align the first and second annular member bores (5)(9) to provide a first fluid flow passageway (12).

With reference to FIGS. 4I and 5D in particular, the second annular member (8) includes a second annular member wall (33) having opposing second annular member wall outer and inner surfaces (34)(35), whereby the second annular member wall inner surface (35) defines the second annular member bore (9). As to particular embodiments, the second annular member wall (33) may be substantially cylindrical or cylindrical and correspondingly, may have a substantially circular or circular cross section; thus, the second annular member wall inner surface (35) may define a second annular member bore (9) having a substantially circular or circular cross section. However, it is also herein contemplated that the second annular member wall (33) may define any shape or configuration useful for connecting the sanitary fitting (1) to a bag (3) and/or a fluid conduit (2) for the transfer of fluid via the sanitary fitting (1) between the fluid conduit (2) and the bag (3).

Again with reference to FIGS. 4I and 5D expressly, as to particular embodiments, the second annular member wall (33) can include an annular opening (36) disposed between the second annular member wall outer and inner surfaces (34)(35), whereby the annular opening (36) can extend axially inwardly from the second annular member first end (10). Upon coupling of the second annular member (8) and a valve (37), the annular opening (36) can receive and/or house a valve-biasing member (38) which biases the valve (37) toward a valve closed position (39) in which the valve (37) sealably occludes a fluid flow path (40) which includes the first fluid flow passageway (12) to provide a fluid flow path closed condition, as detailed further below.

Now referring primarily to FIGS. 5B and 5D, as to particular embodiments, the second annular member wall outer surface (34) can have a greater circumference proximate or at the second annular member first end (10) relative to the second annular member second end (11) or said another way, the second annular member wall outer surface (34) can have a lesser circumference proximate or at the second annular member second end (11) relative to the second annular member first end (10).

Now referring primarily to FIG. 5D, as to particular embodiments, the second annular member wall inner surface (15) can define a parabolic port (41) having a parabolic-shaped cross section with a vertex located at the second annular member second end (11), whereby the parabolic port (41) may facilitate optimal fluid flow though the sanitary fitting (1).

Again referring primarily to FIG. 5D, as to particular embodiments, the second annular member wall (33) can further include a groove (30), such as an annular groove (30), radially inwardly extending into the second annular member wall outer surface (34), whereby the groove (30) can be configured to receive a mating tongue (29) of the first annular member (4) upon coupling of the first and second annular members (4)(8). Of course, the reverse is also contemplated, such that a tongue can radially outwardly extend from the second annular member wall outer surface (34) and accordingly, the first annular member (4) can include the mating groove.

Now referring primarily to FIGS. 4I and 5D, as to particular embodiments, the second annular member wall outer surface (34) can include a second annular member first shoulder (42), which may be configured to receive or seat a seal (32), such as an annular seal (for example, an o-ring), upon coupling of the first and second annular members (4)(8), whereby the seal (32) can function to sealably engage the first and second annular members (4)(8).

Again referring primarily to FIGS. 4I and 5D, as to particular embodiments, the second annular member wall outer surface (34) can further include a second annular member second shoulder (43), whereby upon coupling of the first and second annular members (4)(8), the second annular member second shoulder (43) can be configured to axially receive the first annular member first end (6) to provide a flush or even junction or whereby the first and second annular member wall outer surfaces (14)(34) can be radially flush or even at the junction. The second annular member second shoulder (43) can be disposed radially outwardly from the second annular member first shoulder (42) in axially offset relation such that the second annular member second shoulder (43) disposes closer to the second annular member first end (10) relative to the second annular member first shoulder (42).

Valve

Now referring primarily to FIG. 6A through FIG. 9D, the sanitary fitting (1) further includes a valve (37) coupled to the second annular member (8), whereby the valve (37) can be operable to interrupt fluid flow through a fluid flow path (40) which includes the first fluid flow passageway (12) to provide a fluid flow path closed condition. For example, the valve (37) can dispose within a fluid flow path (40) which flows through a fluid conduit (2) coupled to a bag (3) via the sanitary fitting (1), the valve (37) correspondingly operable to interrupt fluid flow between the fluid conduit (2) and the bag (3).

Now referring primarily to FIG. 6A through FIG. 7D, the valve (37) can be included within a valve assembly (44), whereby the valve assembly (44) can further include a sleeve (45), which may be annular, concentrically disposed about the valve (37). The valve assembly (44) can define a second fluid flow passageway (46), whereby the fluid flow path (40) can include both the first and second fluid flow passageways (12)(46) through which fluid can flow between a fluid conduit (2) and a bag (3).

At least one fluid-tight seal can exist between the valve outer surface (47) of the valve (37) and a sleeve inner surface (48) of the sleeve (45), whereby as to particular embodiments, the fluid-tight seal may be facilitated by an annular seal (32) (such as an o-ring).

The valve (37) can be axially movable within the sleeve (45) between (i) a valve closed position (39) in which the valve (37) sealably occludes the second fluid flow passageway (46) and correspondingly the fluid flow path (40) (as shown in FIGS. 8A through 8E) and (ii) a valve open position (49) in which the valve (37) allows fluid to flow through the second fluid flow passageway (46) and thus within the fluid flow path (40), for example between a fluid conduit (2) and a bag (3) (as shown in FIG. 2A).

The valve assembly (44) can further include a valve-biasing member (38) which biases the valve (37) toward the valve closed position (39). As but one illustrative example, the valve-biasing member (38) can be configured as a resiliently compressible member, such as a spring (for example, a coil spring or a helical spring). As but a second illustrative example, the valve-biasing member (38) can be configured as a resiliently flexible member (not shown).

Figure 8D:
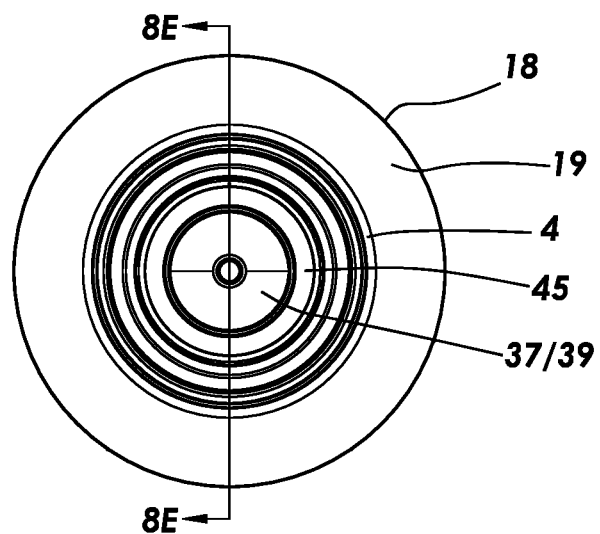
FIG. 8D shows a front view of the particular embodiment of the sanitary fitting shown in FIG. 8A.
Figure 8E:
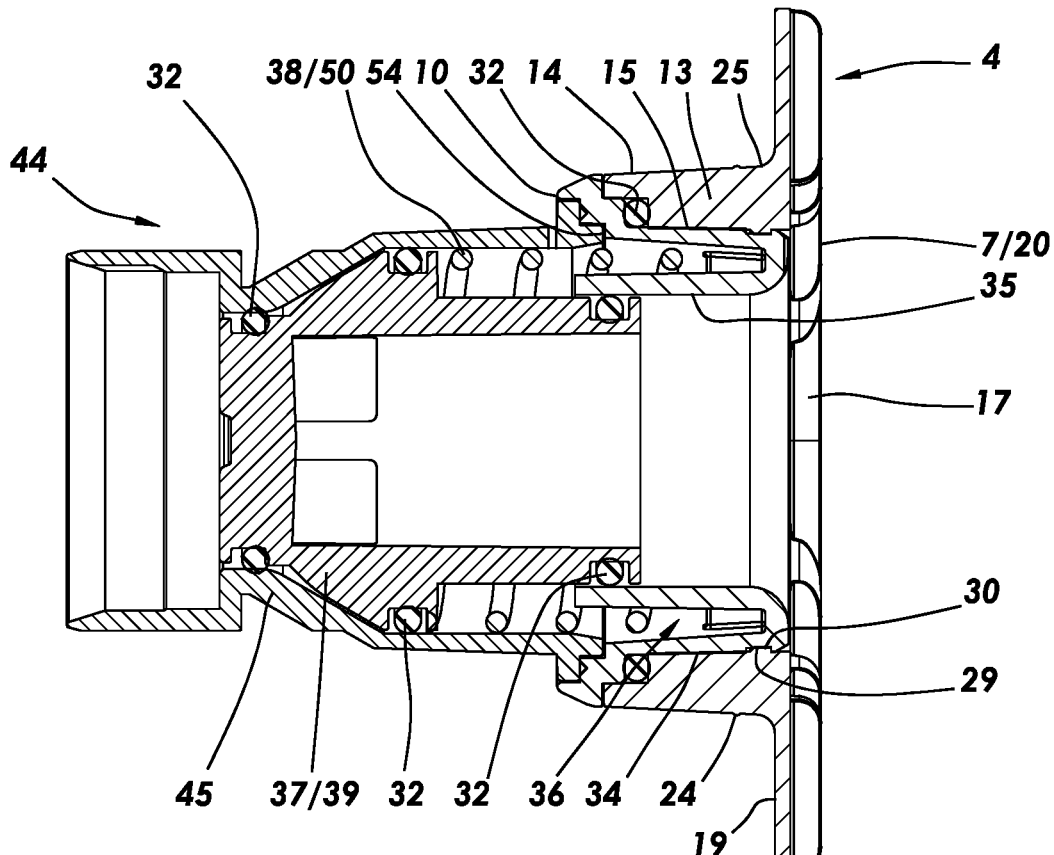
FIG. 8E shows a cross-sectional view of the particular embodiment of the sanitary fitting shown in FIG. 8D.

Regarding the resiliently compressible member (38), when in a non-compressed condition (50) (as shown in FIG. 8E), which is the normal biased condition, the resiliently compressible member (38) can bias the valve (37) toward the valve closed position (39). Upon forcible urging, the resiliently compressible member (38) can be compressed toward a compressed condition (51) (as shown in FIG. 2A), allowing the valve (37) to axially travel within the sleeve (45) toward the valve open position (49).

Now referring primarily to FIGS. 1A through 3, and FIGS. 9A through 9D, the resiliently compressible member (38) can be compressed toward the compressed condition (51) upon forcible urging resulting from axial connection of a female coupler (52) with the valve assembly (44), thus allowing the valve (37) to axially travel within the sleeve (45) toward the valve open position (49). In use, a fluid conduit (2) can be coupled to the female coupler (52), for example via a barbed fitting (53) of the female coupler (52); accordingly, upon axial connection of the female coupler (52) with the valve assembly (44) and resultant travel of the valve (37) toward the valve open position (49), fluid can flow within the fluid flow path (40) between the fluid conduit (2) and a bag (3).

In contrast to conventional "quick release" connectors, the instant valve-biasing member (38) is disposed external to or outside of the second fluid flow passageway (46) and correspondingly, external to or outside of the fluid flow path (40). Correspondingly, fluid flowing within the fluid flow path (40) does not contact the valve-biasing member (38), which may be advantageous for a plurality of reasons, including elimination of a potential substrate for biofilm growth within the fluid flow path (40) and elimination of a physical impediment to fluid flow within the fluid flow path (40).

Structurally, the valve-biasing member (38) can concentrically dispose about the valve (37); following, the valve-biasing member (38) can dispose between a valve outer surface (47) of the valve (37) and a sleeve inner surface (48) of the sleeve (45).

In use, the valve assembly (45) couples to the second annular member (8) to facilitate sterile transfer of fluid between a fluid conduit (2) and a bag (3). For example, a sleeve second end (54) of the sleeve (45) can be hermetically sealed to the second annular member first end (10), for example via a welding process. Following, for such a coupling, the sleeve second end (54) can be disposed proximate the second annular member first end (10) and engaged via matable geometry, and a welder can provide heat (typically) to weld the sleeve second end (54) to the second annular member first end (10). This weld can be impermeable; thus, once the sanitary fitting (1) has been coupled to the bag (3), fluid can be transferred through the sanitary fitting (1), either into or out of the bag (3), while maintaining the sterility within the bag (3).

To facilitate welding, the second annular member first end (10) can be formed from a second material (55), typically a polymeric material, preselected based on its weldability to the valve assembly (44). As but one illustrative, non-limiting example, the second material (55) can be polypropylene, which may be useful for welding to a valve assembly (45) such as a SERIESLOCK™, available from Eldon James Corporation, 10325 East 47$^{th}$ Avenue, Denver Colo., USA.

Now referring primarily to FIG. 8E, as mentioned above, upon coupling of the valve assembly (44) to the second annular member (8), the valve-biasing member (38) can be received and/or housed within the annular opening (36) disposed between the second annular member wall outer and inner surfaces (34)(35).

Use

As to particular embodiments, the first and second annular members (4)(8) can be discrete from one another, meaning separate entities or distinct entities.

In use, the first and second annular members (4)(8) can be coupled together to axially align the first and second annular member bores (5)(9) to provide the first fluid flow passageway (12). As to particular embodiments, the second annular member second end (11) can be axially inserted into the first annular member bore (5) via the first annular member first end (6), and the first and second annular members (4)(8) can snap together for a friction fit, which may be facilitated by a mating tongue (29) and groove (30) construct, as detailed above. Also as detailed above, the first and second annular members (4)(8) can be sealably engaged via a seal (32), such as an o-ring, disposed between the first annular member shoulder (31) and the second annular member first shoulder (42).

As to particular embodiments, the method can further include coupling the first annular member (4) and in particular, the flange first face (19), to a bag (3).

As to particular embodiments, the method can further include coupling the sanitary fitting (1) and in particular, the valve assembly (44), to a female coupler (52). Advantageously, the valve assembly (44) and correspondingly, the sanitary fitting (1), can be relatively easily and securely connected to the female coupler (52) and correspondingly, the fluid conduit (2), and yet relatively easily intentionally disconnected.

As to particular embodiments, the method can further include coupling a fluid conduit (2) to the female coupler (52).

For connection of the sanitary fitting (1) and the female coupler (52), as to particular embodiments, a catch assembly (56) (or catch) can be movably coupled to the female coupler (52) and a catch-receiving element (57) can be coupled to the valve assembly (44). Upon connection of the female coupler (52) and the valve assembly (44), the catch assembly (56) engages with the catch-receiving element (57) to fix an axial position of the female coupler (52) in relation to the valve assembly (44), thereby releasably coupling the components.

For disconnection, as to particular embodiments, a release element (58) can be movably coupled to the female coupler (52), whereby travel of the release element (58) along or over the outer surface of the female coupler (52) disengages the catch assembly (56) from the catch-receiving element (57) to disconnect the valve assembly (44) from the female coupler (52).

Method of Making

A method of making a particular embodiment of the sanitary fitting (1) can include providing a first annular member (4) having a first annular member bore (5) extending between first annular member first and second ends (6)(7), the first annular member second end (7) terminating in a flange (17) radially outwardly extending therefrom, the flange (17) comprising a substantially planar flange first face (19); providing a second annular member (8) having a second annular member bore (9) extending between second annular member first and second ends (10)(11), the second annular member (8) couplable to the first annular member (4) to axially align the first and second annular member bores (5)(9) to provide a first fluid flow passageway (12); and coupling a valve (37) to the second annular member (8), the valve (37) operable to interrupt fluid flow through a fluid flow path (40) which includes the first fluid flow passageway (12).

The method of making the sanitary fitting (1) and associated components can further include providing additional elements as described above and in the claims.

As to particular embodiments, one or more of the above components can be formed from an antibacterial material(s).

As to particular embodiments, one or more of the above components can be formed entirety from non-metallic material(s).

Additionally, the components can be produced from any of a wide variety of processes depending upon the application, such as press molding, injection molding, fabrication, machining, printing, additive printing, or the like, or combinations thereof, as one piece or assembled from a plurality of pieces into a component.

As to particular embodiments, one or more of the above components can be disposable or reusable, depending upon the application.

As to particular embodiments, one or more components of the instant invention can be similar to or the same as one or more components disclosed in U.S. Pat. Nos. 10,173,046 and 10,293,150, and United States Patent Application Publication Nos. 2018/0304066, 2019/0269901, 2020/0188651, each of which is hereby incorporated by reference herein in its entirety. For example, the instant the valve assembly (44) can be similar to or the same as the disclosed male coupler, the instant female coupler (52) can be similar to or the same as the disclosed female coupler, the instant resiliently compressible member (38) can be similar to or the same as the disclosed resiliently compressible member, the instant resiliently flexible member can be similar to or the same as the disclosed resiliently flexible member, the instant catch can be similar to or the same as the disclosed catch, the instant catch-receiving element can be similar to or the same as the disclosed catch-receiving element, and the instant release element can be similar to or the same as the disclosed release element.

As to particular embodiments, one or more components of the instant invention can be similar to or the same as one or more components disclosed in U.S. Pat. Nos. 10,350,401 and 10,583,281, each of which is hereby incorporated by reference herein in its entirety. For example, the instant catch assembly (56) can be similar to or the same as the disclosed catch assembly, and the instant catch-receiving element (57) can be similar to or the same as the disclosed catch-receiving element.

As can be easily understood from the foregoing, the basic concepts of the present invention may be embodied in a variety of ways. The invention involves numerous and varied embodiments of a sanitary fitting and methods for making and using such a sanitary fitting, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "coupler" should be understood to encompass disclosure of the act of "coupling"—whether explicitly discussed or not—and, conversely, were there effectively disclosure of the act of "coupling," such a disclosure should be understood to encompass disclosure of a "coupler" and even a "means for coupling." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Further, for the purposes of the present invention, the term "coupled" or derivatives thereof can mean indirectly coupled, coupled, directly coupled, connected, directly connected, or integrated with, depending upon the embodiment.

Thus, the applicant(s) should be understood to claim at least: i) each of the sanitary fittings herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A sanitary fitting for coupling a fluid conduit to a bag to facilitate sterile transfer of fluid therebetween, comprising:
    a first annular member having a first annular member bore extending between first annular member first and second ends, said first annular member second end terminating in a flange radially outwardly extending therefrom, said flange comprising a substantially planar flange first face;
    a second annular member having a second annular member bore extending between second annular member first and second ends, said second annular member couplable to said first annular member to axially align said first and second annular member bores to provide a first fluid flow passageway; and
    a valve coupled to said second annular member, said valve operable to interrupt fluid flow through a fluid flow path which includes said first fluid flow passageway.

2. The sanitary fitting of claim 1, said first annular member further comprising a first annular member wall having opposing first annular member wall outer and inner surfaces, said first annular member wall inner surface defining said first annular member bore.

3. The sanitary fitting of claim 2, wherein said flange first face disposes toward said first annular member first end.

4. The sanitary fitting of claim 3, said first annular member further comprising an annular lip radially outwardly extending from said first annular member wall outer surface proximate said flange first face.

5. The sanitary fitting of claim 3, wherein a flange second face which opposes said flange first face is substantially planar.

6. The sanitary fitting of claim 5, further comprising at least one protrusion axially outwardly extending from said flange second face.

7. The sanitary fitting of claim 6, said protrusion comprising a linear protrusion.

8. The sanitary fitting of claim 2, said first annular member wall comprising one of a tongue radially outwardly extending from said first annular member wall inner surface or a groove radially inwardly extending into said first annular member wall inner surface.

9. The sanitary fitting of claim 8, said second annular member further comprising a second annular member wall having opposing second annular member wall outer and inner surfaces, said second annular member wall inner surface defining said second annular member bore; and
   said second annular member wall comprising one of a groove radially inwardly extending into said second annular member wall outer surface or a tongue radially outwardly extending from said second annular member wall outer surface.

10. The sanitary fitting of claim 1, further comprising a valve assembly which includes said valve and a sleeve concentrically disposed about said valve, said valve assembly defining a second fluid flow passageway.

11. The sanitary fitting of claim 10, wherein said valve is axially movable within said sleeve between valve closed and open positions.

12. The sanitary fitting of claim 11, said valve assembly further comprising a valve-biasing member which bias said valve toward said valve closed position.

13. The sanitary fitting of claim 12, wherein said valve-biasing member disposes outside of said second fluid flow passageway.

14. The sanitary fitting of claim 13, wherein said valve-biasing member disposes outside of said fluid flow path.

15. The sanitary fitting of claim 14, said second annular member further comprising a second annular member wall having opposing second annular member wall outer and inner surfaces, said second annular member wall inner surface defining said second annular member bore; and
   said second annular member wall comprising an annular opening disposed between said second annular member wall outer and inner surfaces, said annular opening extending axially inwardly from said second annular member first end;
   wherein upon coupling of said valve assembly and said second annular member, said valve-biasing member is received within said annular opening.

16. The sanitary fitting of claim 1, wherein said flange first face is configured to be sealed to a bag wall interior surface of said bag.

17. The sanitary fitting of claim 10, wherein a sleeve second end of said sleeve is configured to be sealed to said second annular member first end.

18. The sanitary fitting of claim 10, wherein:
   said flange first face is formed from a first material preselected based on its weldability to a bag wall of said bag;
   a sleeve second end of said sleeve is formed from a second material preselected based on its weldability to said second annular member first end; and
   wherein said first and second materials are the same.

19. The sanitary fitting of claim 10, wherein:
   said flange first face is formed from a first material preselected based on its weldability to a bag wall of said bag;
   a sleeve second end of said sleeve is formed from a second material preselected based on its weldability to said second annular member first end; and
   wherein said first and second materials are different.

20. The sanitary fitting of claim 1, wherein said first annular member is discrete from said second annular member.

* * * * *